United States Patent [19]

Shuenn-tzong

[11] 4,361,648
[45] Nov. 30, 1982

[54] COLOR FIXED CHROMOGENIC ANALYTICAL ELEMENT

[75] Inventor: Chen Shuenn-tzong, Elkhart, Ind.

[73] Assignee: Miles Laboratories, Inc., Elkhart, Ind.

[21] Appl. No.: 292,345

[22] Filed: Aug. 13, 1981

[51] Int. Cl.$^3$ .................. C12Q 1/26; C12Q 1/28; C12Q 1/44; C12Q 1/54; C12Q 1/60; C12Q 1/62; C12Q 1/32

[52] U.S. Cl. .................................. 435/10; 435/11; 435/14; 435/19; 435/25; 435/26; 435/28; 435/805; 435/810; 23/230 B; 422/56

[58] Field of Search .................. 435/10, 11, 14, 18, 435/19, 25, 26, 28, 805, 810; 23/230 B; 422/56

[56] References Cited

U.S. PATENT DOCUMENTS

| | | | |
|---|---|---|---|
| 3,298,789 | 1/1967 | Mast | 435/14 |
| 4,038,485 | 7/1977 | Johnston et al. | 435/11 |
| 4,211,845 | 7/1980 | Genshaw et al. | 435/14 |
| 4,273,868 | 6/1981 | Walter | 435/14 |
| 4,303,753 | 12/1981 | Lam | 435/14 |

Primary Examiner—Esther M. Kepplinger
Attorney, Agent, or Firm—Roger N. Coe

[57] ABSTRACT

Analytical element method of making the analytical element and process for determining an analyte in a body fluid sample are disclosed. More particularly, the method of preparing the element comprises the steps of: (a) impregnating a carrier with a first solution, having a pH not greater than about 2.5, which comprises a polymeric mordant and a tetraalkylbenzidine dihydrochloride, in a molar concentration greater than that of the polymeric mordant in an aqueous solvent and drying the carrier; (b) impregnating the carrier of (a) with a solution, having a pH of at least about 7.0, which comprises an analyte-responsive component in an aqueous solvent and drying the carrier. Optionally, there can be added the step of impregnating the carrier of (b) with a solution of a semi-permeable polymer in an organic solvent and drying the carrier.

22 Claims, No Drawings

COLOR FIXED CHROMOGENIC ANALYTICAL ELEMENT

BACKGROUND OF THE INVENTION

1. Field of the Invention

The present invention relates generally to the field of diagnostic tests and, more particularly, to test devices and elements useful in the qualitative and quantitative determination of an analyte using a composition which includes a tetraalkylbenzidine indicator.

2. Brief Description of the Prior Art

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976).

The chromogenic indicator o-tolidine has been used for some time in test compositions, but provides results which are subject to reduction of the oxidized indicator by interfering substances, such as ascorbic acid. Further, the safety of o-tolidine has been questioned. British published patent specifications 1,464,359 and 1,464,360 disclose the use of 3,3',5,5'-tetramethylbenzidine and similar compounds and their use in the detection and determination of hydrogen peroxide or of constituents which react to form peroxides.

U.S. Pat. No. 4,273,868, commonly assigned herewith, discloses a composition, a test device, method of making the test device and process for determining glucose in a sample. The test composition comprises glucose oxidase, a peroxidatively active substance, such as peroxidase, a stabilizing agent and a 3,3',5,5'-tetraalkylbenzidine indicator in an amount sufficient rapidly to produce, upon contact of the test means with a predetermined amount of a glucose-containing sample, a stable colored reaction product believed to comprise reduced and oxidized forms of said indicator in stable equilibrium. Preferably, the 3,3',5,5'-tetramethylbenzidine is present in a concentration of at least about 2.6 millimoles per thousand International Units of glucose oxidase activity. One of the disclosed stabilizing agents is an interpolymer of methylvinyl ether and maleic anhydride, marketed commercially as Gantrez AN-139 by GAF Corporation. The test devices are prepared by a two-dip impregnation process where the 3,3',5,5'-tetraalkylbenzidine is impregnated in the second dip using a solution thereof prepared in an organic solvent.

SUMMARY OF THE INVENTION

Test devices prepared as taught by the prior art have experienced problems of color deterioration, have required high reagent concentrations (with attendant high cost) and/or have been susceptible to providing imprecise readings because of dependence on user technique. For example, certain devices lose much of their reacted indicator during required washing procedures with a resultant change in reading accuracy.

These problems, having now been recognized, are all diminished or overcome in the analytical element of the present invention. This improvement has been achieved by a method of preparing the element, which method comprises the steps of:

(a) impregnating a carrier with a first solution, having a pH not greater than about 2.5, which comprises a polymeric mordant and a tetraalkylbenzidine dihydrochloride, in a molar concentration greater than that of the polymeric mordant, in an aqueous solvent and drying the carrier;

(b) impregnating the carrier of (a) with a solution, having a pH of at least about 7.0, which comprises an analyte-responsive component in an aqueous solvent and drying the carrier.

Likewise there is provided an analytical element and method for the determination of an analyte in a fluid sample which comprises contacting a sample with the analytical element according to the invention and observing any resultant color change. The colored reaction product is produced within a time period of not more than about 60 seconds and, more specifically, between about 10 and 30 seconds after contact of the analytical element with the body fluid sample to be tested.

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

ANALYTE-RESPONSIVE COMPONENT

The analyte-responsive component comprises those reagents which interact with the analyte and/or resulting products thereof to produce an oxidizing substance, e.g., hydrogen peroxide. In the presence of a peroxidatively active substance, which is one reagent of the analyte-responsive component, the oxidizing substance oxidizes the tetraalkylbenzidine to produce a detectable species thereof.

The detection and quantitative determination of hydrogen peroxide and compounds yielding hydrogen peroxide are of importance in many areas, for example, in the detection of hydrogen peroxide produced in the enzymatic assay of substances such as glucose, cholesterol, uric acid, amino acids like xanthine, etc. by the activity of enzymes such as glucose oxidase, cholesterol oxidase (optionally also including cholesterol ester hydrolase), uricase, amino acid oxidases like xanthine oxidase, etc. in the presence of oxygen. The quantity of enzyme substrate present in a sample is determinable from the amount of hydrogen peroxide produced and detected.

Known compositions for detecting and/or quantifying hydrogen peroxide in such systems generally comprise a substance having peroxidative activity, e.g., peroxidase and peroxidase-like substances, and material which undergoes a detectable change (generally a color change) in the presence of hydrogen peroxide and the peroxidative substance. A complete list of the prior art which describes such compositions is too extensive for presentation here. However, a few representative patents which describe such materials are: U.S. Pat. Nos. 2,921,309, 2,981,606, 3,349,006, 3,092,465, 3,558,435, 3,595,755, 3,627,697, 3,627,698, 3,630,847, 3,654,179, 3,654,180 and 3,853,470.

Preferably, a dual enzyme system is present: one or more enzymes transform the analyte to produce hydrogen peroxide, whereas the other enzyme has peroxidative activity.

Peroxidatively active substances are enzyme-like in that they catalyze the redox reaction between peroxides and benzidine, o-tolidine, 3,3',5,5'-tetramethylbenzidine, 2,7-diaminofluorene or similar indicator substances, thereby producing a detectable response such as a color change. Hemoglobin and its derivatives are typical of such "peroxidatively active" substances because they behave in a manner similar to the behavior of the enzyme peroxidase. Such substances have also been referred to as pseudoperoxidases. As stated at column 5, line 56 to column 6, line 11 of U.S. Pat. No. 4,089,747, a peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms and may be producted by fermentation. Certain synthetic peroxidases, such as those disclosed by Theorell and Maehly in Acta. Chem. Scand, Vol. 4, pages 422–434 (1950), are also satisfactory for use in $H_2O_2$ detection systems. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides. Other substances which are not enzymes but which demonstrate peroxidative activity are: iron sulfocyanate, iron tannate, ferrous ferrocyanide, and chromic salts (such as potassium chromic sulfate).

TETRAALKYLBENZIDINES

The various benzidine indicators which can be used include the 3,3',5,5'-tetraalkylbenzidines, wherein alkyl is a $C_1$–$C_4$ alkyl, and 3,3',5,5'-tetramethylbenzidine is particularly preferred. Others which can also be used include 3-methyl, 3'-methyl, 5-ethyl, 5'-ethyl benzidine and 3,3',5,5'-tetraethylbenzidine. As can be seen from these examples, the four alkyl groups can be the same or different.

The 3,3',5,5'-tetraalkylbenzidines are preferred over other known indicators because of, among other things, their freedom from carcinogenicity.

Preferably the tetraalkylbenzidine dihydrochloride is present in a concentration of from about 1.0 to about 2.0 percent of the composition on a weight to weight basis.

POLYMERIC MORDANT

Suitable polymeric mordants which can be used include poly(carboxylic acids) having the formula:

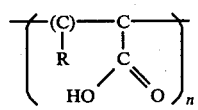

wherein R is a $C_1$–$C_{18}$ alkyl or amide, and n is an integer from 2 to the total number of repeating units of the polymer. Examples include acrylic acid and acrylamide copolymer.

Other polymeric mordants which can be used are copolymeric anhydrides having the formula:

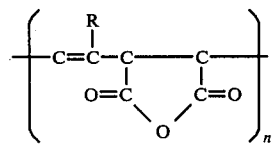

wherein R is $C_1$–$C_{18}$ alkyl, ether, acetate or benzyl and n is an integer from 2 to the total number of repeating units of the polymer. Examples include methyl vinyl ether maleic anhydride copolymer; vinyl acetate maleic anhydride copolymer; ethylene maleic anhydride copolymer; octadecyl vinyl ether maleic anhydride copolymer; and styrene maleic anhydride copolymer.

The polymeric mordant is preferably present in a concentration of from about 0.5 to about 0.75 percent of the composition on a weight to weight basis.

CARRIER

The term carrier refers to matrices which are insoluble in and maintain their structural integrity when exposed to physiological or other liquid to be tested. Suitable matrices when can be used include paper, cellulose, wood, synthetic resin fleeces, glass fiber, nonwoven and woven fabrics, gelatin, various organic polymers, such as polypropylene, and other organic materials well known as film formers to those skilled in the art. For convenience, the carrier can be suitably attached to an insoluble support or handle member which can be made from polystyrene.

ELEMENT PREPARATION

The test device is prepared by a process which comprises (a) impregnating a carrier with a first solution, having a pH not greater than about 2.5, which comprises a polymeric mordant and a tetraalkylbenzidine dihydrochloride, in a molar concentration greater than that of the polymeric mordant, in an aqueous solvent and drying the carrier; and (b) impregnating the carrier of (a) with a solution, having a pH of at least 7.0, which comprises an analyte-responsive component in an aqueous solvent and drying the carrier. This method may comprise the additional step of (c) impregnating the carrier of (b) with a solution of a semi-permeable polymer, such as ethyl cellulose, in an organic solvent and drying the carrier. The organic solvent preferably includes toluene. Particularly preferred is an organic solvent which includes toluene and ethanol. Where the solvent consists essentially of toluene and ethanol, the toluene is from about 80 to about 95 percent of the solvent and the ethanol is from about 5 to about 20 percent of the solvent, the toluene and ethanol being together 100 percent.

When the test composition is to be used for detecting an analyte in whole blood, the impregnated carrier matrix is advantageously covered, in accordance with step (c) of the above-described method with a semipermeable transparent coating or film of ethyl cellulose or other suitable material. This can be accomplished, for example, by applying a layer of ethyl cellulose dissolved in a selected organic solvent(s) to the surface of the impregnated carrier and then removing the solvent by evaporative drying.

Test devices in the form of treated carriers are often stored for considerable periods of time before use, and it is therefore desirable that the reagents chosen are not easily auto-oxidizable in air. Advisably, the test devices should be protected from exposure to light and in some cases it is desirable to keep them sealed in a moisture repellent package which is opened only for removal of one or more test devices shortly before use.

If desirable, a carrier matrix can be treated with a background dye of a particular color, such as yellow, so that the color produced by reaction with glucose is blended with the background color to produce varying tints which correspond to the concentration of glucose present in the fluid or liquid being tested. It may be especially desirable to dye the carrier yellow when the colored reaction product is blue.

ANALYTICAL PROCEDURE

The test device is advantageously used by momentarily dipping it in a test sample or by otherwise introducing a test sample into the carrier matrix, whereby a detectable color change results when glucose is present. The volumetric capacity of the carrier serves to limit the amount of sample absorbed thereby and to which the test means incorporated therewith is exposed. Any excess sample can be removed by washing or blotting the carrier to thereby limit the amount of sample tested to the volume thereof which has actually entered the carrier matrix. The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids. The test device can be used in the same way when samples of plasma, serum or other body fluids are tested.

For highly precise determinations of glucose concentration, photoelectric, colorimetric or spectrophotomeric methods can be employed to determine color indication. The GLUCOMETER TM reflectance colorimeter (Ames Company, Division of Miles Laboratories, Inc.) is a portable instrument designed to quantitatively measure whole blood glucose when used in conjunction with DEXTROSTIX ® reagent strips (Ames Company, Division of Miles Laboratories, Inc.) and elements prepared in accordance with the present invention. The GLUCOMETER reflectance colorimeter measures the light reflected from the surface of the reacted test device matrix and converts this measurement, by means of electronic circuitry, to a reading on a precisely calibrated meter scale on the instrument which is capable of indicating blood glucose within the range of 10 to 400 milligrams (mg)/100 milliliter (ml). The higher blood glucose level, the darker the strip and the less light reflected. Conversely, the lower the blood glucose level the lighter the strip and the more light reflected. The colorforming test means or device described herein has been found to be especially useful in that it provides a unique color response which can be determined by the GLUCOMETER reflectance colorimeter in a fashion similar to that of DEXTROSTIX reagent strips. Alternatively, semiquantitative results can be obtained using the analytical element of the present invention by comparing the color produced with a panel of standard colors obtained with known concentrations of analyte employing the same indicator.

The relationship between K (the absorption coefficient of the specimen) and the concentration of the absorbing species (i.e. analyte) is given by the Kubelka-Monk equation which is provided, along with a detailed discussion of reflectance spectrophotometry in Kortumi, G., *Reflectance Spectroscopy*, Springer-Verlag Inc., New York, 1969.

The term K/S, used in the example, is a ratio that is defined by the formula $(1-R)^2/2R$, wherein R is reflectance and S is the scattering coefficient of the particular carrier used. Therefore, K/S is proportional to the amount of chromogen formed by the reaction. Readings in the examples were taken at the wavelengths indicated.

EXAMPLES

The examples shown are merely illustrative and not to be construed as a limitation of the invention. One skilled in the art will be able to make such variations, substitutions and changes in the ingredients and parameters as may seem desirable. Horseradish peroxidase, glucose oxidase, cholesterol oxidase and cholesterol esterase used in the examples were obtained from the Research Products Division, Miles Laboratories, Inc., Elkhart, IN. Gantrez AN-139 and polyvinylpyrrolidone (PVP) were obtained from GAF Corp., Chemical Products, N.Y., N.Y. The activity of the enzyme preparation is measured by the number of units of activity per milligram of dry weight. The Commission on Enzymes of the International Union of Biochemistry has defined an International Unit (I.U.) of enzyme activity as 1 micromole ($\mu$mol) of substrate utilized per minute under specified conditions of pH and temperature control.

EXAMPLE I

Analytical Element for Glucose Assay

In the experiments reported by this example analytical elements were prepared by the method according to the invention and tested for their ability to quantitatively determine, as read by reflectance, the presence of glucose in a liquid sample. In general, by converting 3,3',5,5'-tetramethylbenzidine (TMB) free base to the TMB.2HCl salt, it was possible to impregnate the TMB in an aqueous dip. During the course of these experiments it was observed that it is impossible to impregnate the TMB free base in an aqueous pH 7 medium with the quantity required for the reaction. Gantrez AN-139, a polycarboxylic anion (chemically it is the interpolymer of methyl vinyl ether and maleic anhydride), was added with TMB.2HCl in the first dip. The Gantrez behaves as a dye mordant, so forming a complex, in the system, thereby protecting final colored reaction product. This first dip was followed by impregnating the enzymes and buffer as the second dip. Ethyl cellulose in toluene was used as the third dip. Paper strips prepared with this protocol greatly reduced the criticality of the washing technique used in glucose measurement.

Element Preparation

The solutions used in preparing the glucose specific element contained the following components:

| Ingredient | Quanity/100 ml |
|---|---|
| First Solution | |
| TMB.2HCl | 1.5 grams (g) |

| Ingredient | Quanity/100 ml |
|---|---|
| Gantrez AN-139 | 0.75 g |
| Distilled Water | 100 ml |
| Second Solution | |
| Peroxidase | 1 g |
| Glucose Oxidase | $18 \times 10^3$ IU |
| Polyvinyl pyrrolidone | 2.8 g |
| Tris hydroxymethyl aminomethane (Tris)-Malonate Buffer | pH = 7.4 |
| Distilled Water | 100 ml |
| Third Solution | |
| Ethyl cellulose | 2.0 g |
| Toluene | 100.0 ml |

Reagent-containing Whatman 3MM filter paper (Whatman, Inc., Clifton, N.J.) is prepared by (a) impregnating sheets of the paper to saturation with the first solution and drying the paper at 60° Centigrade (C.) for 10 minutes; (b) impregnating the paper of (a) to saturation with the second solution and drying at 60° C. for ten (10) minutes; and (c) impregnating the paper of (b) to saturation with the third solution and drying at 35° C. for 10 minutes.

The reagent-containing paper was cut to 0.2 cm (centimeter)×0.4 cm dimensions and fixed to one end of a 0.4 cm×8.25 cm polystyrene film by double-faced adhesive tape, providing devices according to the invention. These were stored with a dessicant in brown glass bottles until used.

Test Solutions

Fresh blood collected into evacuated collection tubes containing ethylene diamine tetraacetic acid (EDTA) was metabolically depleted of glucose by incubation at 37° C. overnight (16~20 hours). The hematocrit was adjusted to about 45%. Various glucose levels were prepared by the addition of a stock (25%) glucose solution [reported in Table 1 as "Actual (mg/dl)"]. Glucose concentrations were assayed by a standard referece method, the Yellow Spring Instrument (YSI) Glucose Analyzer [reported in Table 1 as "Reference (mg/dl)"].

Analytical Procedure

The performance of the reagent device prepared and incubated as above-described was analyzed instrumentally using a device known as the GLUCOMETER ™ reflectance spectrophotometer which yields percent reflectance at 760 nm.

The GLUCOMETER instrument was constructed by the Ames Company Division of Miles Laboratories, Inc., Elkhart, Ind. U.S.A., from whom complete information with respect to structural and performance characteristics are obtainable.

Single drops of whole blood glucose samples were applied to the analytical elements with an eyedropper and allowed to react for 1 minute. At the end of this period the element was washed either with a stream of water from a wash bottle or with a stream of tap water for various time intervals. The strip was then blotted and measured immediately on the GLUCOMETER. All reflectance measurements were converted to K/S values where K/S equals to $(1-R)^2/2R$ in the instrument. The instrument internally converts K/S to the detected clinical values after calibration with commercially available standard solutions.

Results

The results are presented, in digital read-out format, by the GLUCOMETER instrument as milligrams/deciliter (mg/dl) of glucose in the sample under assay [reported in Table 1 as "Experimental (mg/dl)"]. The results obtained for the samples assayed in these experiments are set forth in table form as follows:

TABLE 1

| Actual (mg/dl) | Reference (mg/dl) | Experimental (mg/dl) |
|---|---|---|
| 25 | 26 | 27 |
| 50 | 50 | 46 |
| 70 | 70 | 69 |
| 90 | 92 | 90 |
| 150 | 153 | 155 |
| 200 | 202 | 195 |
| 285 | 290 | 284 |
| 380 | 375 | 390 |

Conclusion

The resultant data shows that elements prepared according to the invention were effective to quantitatively detect the concentration of glucose in a sample with accuracy.

EXAMPLE II

Analytical Element for Cholesterol Assay

In the experiments reported by this example an analytical element was prepared by the method according to the invention and tested for their ability to quantitatively determine, as read by reflectance, the presence of cholesterol in a liquid sample. In general, by converting 3,3',5,5'-tetramethylbenzidine (TMB) free base to the TMB.2HCl it was possible to impregnate the TMB in an aqueous dip. The Gantrez behaves as a dye mordant in the system. This first dip was followed by impregnating the enzymes and buffer as the second dip.

Element Preparation

The solutions used in preparing the cholesterol specific element contained the following components:

| Ingredient | Quantity/100 ml |
|---|---|
| First Solution | |
| TMB.2HCl | 1.5 g |
| Gantrez AN-139 | 0.75 g |
| Distilled Water | 100 ml |
| Second Solution | |
| Peroxidase | 0.1 g |
| Cholesterol Oxidase | 160 I.U. |
| Cholesterol Esterase | 160 I.U. |
| Polyvinyl pyrrolidone | 1.0 g |
| Tris-Malonate Buffer | pH = 7.4 |
| Distilled Water | 100 ml |
| Trypsin Inhibitor | 0.2 g |

Reagent-containing Whatman 3MM filter paper (Whatman, Inc., Clifton, N.J.) is prepared by (a) impregnating sheets of the paper to saturation with the first solution and drying the paper at 60° Centigrade (C.) for 10 minutes; (b) impregnating the paper of (a) to saturation with the second solution and drying at 60° C. for 10 minutes; and (c) impregnating the paper of (b) to saturation with the third solution and drying at 35° C. for 10 minutes.

The reagent-containing paper was cut to 0.2 centimeter×0.4 cm dimensions and fixed to one end of a 0.4 cm × 8.25 cm polystyrene film by double-faced adhesive tape, providing devices according to the invention. These were stored in brown glass bottles until used.

Test Solutions

Three cholesterol control sera (Hyland Diagnostics, Div. of Baxter Travelnol, Chicago, Ill.) contains 194, 285 and 376 mg/dl of cholesterol as determined by the Liebermann-Burchard assay procedure [reported in Table 2 as "Reference (mg/dl)"].

Analytical Procedure

The performance of the reagent devices prepared and incubated as above-described was analyzed instrumentally using a Seralyzer ® reflectance photometer (Ames Company Division of Miles Laboratories, Inc., Elkhart, Ind.) which yields percent reflectance at 560 nanometers (nm) [reported in Table 2 as "Experimental (mg/dl)"]. All reflectance measurements were converted to K/S values were K/S equals to $(1-R)^2/2R$ in the instrument. The instrument internally converts K/S to the detected clinical values after calibration with commercially available standard solutions.

Aliquots (30 μl) which were a 1:9 aqueous dilution of serum containing cholesterol were applied to the analytical elements with a pipette and allowed to react for two (2) minutes. At the end of this period the element was measured by the instrument.

Results

The results are presented, in digital read-out format, by the instrument as milligrams/deciliter (mg/dl) of cholesterol in the sample under assay. The results obtained for the samples assayed in these experiments are set forth in Table 2 as follows:

TABLE 2

| Reference (mg/dl) | Experimental (mg/dl) |
|---|---|
| 194 | 185 |
| 285 | 279 |
| 376 | 380 |

Conclusion

The resultant data shows that elements prepared in accordance with the invention were effective to quantitatively detect the concentration of cholesterol in a sample with accuracy and using tetramethylbenzidine dihydrochloride.

EXAMPLE III

Comparative Susceptibility to Washing

In the experiments reported by this example elements prepared according to the invention were compared with devices prepared according to the teaching of U.S. Pat. No. 4,273,868 and DEXTROSTIX ® reagent strips (Miles Laboratories, Inc., Elkhart, Ind.). The comparison which was made was to evaluate the susceptibility of each of to washing, effected to remove cellular components of whole blood, as reflected in the change in results which are intended to correlate with glucose concentration.

Device Preparations

Elements or devices according to the invention were prepared as described in Example I. The prior art devices of U.S. Pat. No. 4,273,868 were prepared following the preparation described in Example I thereof. DEXTROSTIX reagent strips were obtained as commercially available product.

Test Solutions

Fresh blood collected into evacuated collection tubes containing EDTA was metabolically depleted of glucose by incubation at 37° C. overnight (16~20 hours). The hematocrit was adjusted to about 45%. Various glucose levels were prepared by the addition of a stock (25%) glucose solution. Glucose concentrations were assayed by the Yellow Spring Instrument Glucose Analyzer (YSI).

Analytical Procedure

The performance of the reagent devices as above-described was analyzed instrumentally using a GLUCOMETER ™ reflectance spectrophotometer which yields percent reflectance at 760 nm.

Single drops of glucose samples were applied to the analytical elements with an eyedropper and allowed to react for one minute. At the end of this period the element was washed in one comparison with a stream of water from a wash bottle and in another comparison with a stream of tap water for five seconds. The strip was then blotted and measured immediately on the GLUCOMETER. All reflectance measurements were converted to K/S values where K/S equals to $(1-R)^2/2R$.

Results

The results obtained from these experiments are set forth in Table 3 as follows:

TABLE 3

| Device | Type of Wash | K/S at 200 mg/dl | ΔK/S |
|---|---|---|---|
| DEXTROSTIX ® | Soft, Short Wash (1-2 sec) | 0.869 | 0.138 |
|  | 5 sec, Vigorous | 0.731 |  |
| U.S. Pat. No. 4,273,868 | Soft, Short Wash (1-2 sec) | 0.880 | 0.308 |
|  | 5 sec, Vigorous | 0.572 |  |
| Invention | Soft, Short Wash (1-2 sec) | 1.236 |  |
|  | 5 Seconds, Vigorous | 1.149 | 0.087 |

The above table compares the influence of washing dependence on DEXTROSTIX U.S. Pat. No. 4,273,868 with this invention. Devices prepared according to the teaching of U.S. Pat. No. 4,273,868 show more washing dependence than either DEXTROSTIX ® or this invention, the longer, the more vigorous the washing, the less color. The K/S difference in color gives rise to a variation of about 35 mg/dl glucose with the U.S. Pat. No. 4,273,868 compared to only 15 mg/dl glucose for DEXTROSTIX and this invention. Additionally, although DEXTROSTIX provides acceptable precision, the indicators and solvents used have been questioned as to their safety. By the method of this invention all of the above disadvantages have been overcome.

What is claimed is:

1. A method for preparing an analytical element for determining an analyte in a liquid sample which method comprises the steps of:
   (a) impregnating a carrier with a first solution having a pH not greater than about 2.5, which comprises a polymeric mordant present in a concentration from about 0.5 to about 0.75 percent of the first solution on a weight to weight basis, and a tetraalkylbenzidine dihydrocholoride, with the tetraalkylbenzidine dihydrochloride in a molar concentration greater than that of the polymeric mordant, in an aqueous solvent and drying the carrier;

(b) impregnating the carrier of (a) with a second solution, having a pH of at least about 7.0, which comprises an enzyme and a peroxidatively active substance in an aqueous solvent and drying the carrier.

2. The method of claim 1 wherein the polymeric mordant is a methylvinyl ether maleic anhydride copolymer.

3. The method of claim 1 wherein the polymeric mordant is polyacrylic acid.

4. The method of claim 1 wherein the polymeric mordant is an acrylate-acrylamide copolymer.

5. The method of claim 1 wherein the polymeric mordant is a vinyl acetate-maleic anhydride copolymer.

6. The method of claim 1 wherein the tetraalkylbenzidine dihydrochloride is 3,3′,5,5′-tetramethylbenzidine dihydrochloride.

7. The method of claim 1 wherein the tetraalkylbenzidine dihydrochloride is present in a concentration of from about 1.0 to about 2.0 percent of the first solution on a weight to weight basis.

8. The method of claim 1 wherein the enzyme and the peroxidatively active substance comprises an analyte-specific oxidase and a peroxidatively active substance.

9. The method of claim 1 wherein the enzyme and the peroxidatively active substance comprises glucose oxidase and peroxidase.

10. The method of claim 1 wherein the enzyme and the peroxidatively active substance comprises cholesterol oxidase and peroxidase.

11. The method of claim 1 wherein the enzyme and the peroxidatively active substance comprises cholesterol oxidase, cholesterol esterase and peroxidase.

12. The method of claim 1 wherein the enzyme and the peroxidatively active substance comprises uricase and peroxidase.

13. The method of claim 1 wherein the enzyme and the peroxidatively active substance comprises an amino acid oxidase and peroxidase.

14. The method of claim 1 wherein the enzyme and the peroxidatively active substance comprises xanthine oxidase and peroxidase.

15. The method of claim 1 which comprises the additional step of (c) impregnating the carrier of (b) with a solution of a semi-permeable polymer in an organic solvent and drying the carrier.

16. The method of claim 15 wherein the organic solvent includes toluene.

17. The method of claim 15 wherein the organic solvent includes toluene and ethanol.

18. The method of claim 15 wherein the organic solvent consists essentially of toluene, from about 80 to about 95 percent of the solvent, and ethanol, from about 5 to about 20 percent of the solvent, the toluene and ethanol being together 100 percent.

19. A method for preparing an analytical element for determining glucose in a liquid sample which method comprises the steps of:

(a) impregnating a carrier with a first solution, having a pH not greater than about 2.5, which comprises an interpolymer of methyl vinyl ether and maleic anhydride present in a concentration from about 0.5 to about 0.75 percent of the first solution on a weight to weight basis and 3,3′,5,5′-tetramethylbenzidine dihydrochloride, in a molar concentration greater than that of the interpolymer, in an aqueous solvent and drying the carrier;

(b) impregnating the carrier of (a) with a solution, having a pH of at least about 7.0, which comprises glucose oxidase and peroxidase in an aqueous solvent and drying the carrier; and (c) impregnating the carrier of (b) with a solution of ethyl cellulose in a solvent which consists essentially of toluene, from about 80 to about 95 percent of the solvent, and ethanol, from about 5 to about 20 percent of the solvent, the toluene and ethanol being together 100 percent, and drying the carrier.

20. An analytical element for determining an analyte in a liquid sample, which element is prepared by the method of any of claims 1, 15 or 19.

21. A method for determining an analyte in a liquid sample which comprises contacting the sample with an analytical element prepared by the method of any of claims 1, 15 or 19 and observing any detectable response.

22. A method for preparing an analytical element for determining cholesterol in a liquid sample which method comprises the steps of:

(a) impregnating a carrier with a first solution having a pH not greater than about 2.5, which comprises an interpolymer of methyl vinyl ether and maleic anhydride present in a concentration from about 0.5 to about 0.75% of the first solution on a weight to weight basis and 3,3′,5,5′-tetramethylbenzidine dihydrocholoride, with the 3,3′,5,5′-tetramethylbenzidine in a molar concentration greater than that of the interpolymer, in an aqueous solvent and drying the carrier;

(b) impregnating the carrier of (a) with a solution, having a pH of at least about 7.0, which comprises cholesterol oxidase, cholesterol esterase and peroxidase in an aqueous solvent and drying the carrier; and (c) impregnating the carrier of (b) with a solution of ethyl cellulose and a solvent which consists essentially of toluene, from about 80 to about 95% of the solvent, and ethanol, from about 5 to about 20% of the solvent, the toluene and ethanol being together 100%, and drying the carrier.

* * * * *

UNITED STATES PATENT AND TRADEMARK OFFICE
CERTIFICATE OF CORRECTION

PATENT NO. : 4,361,648

DATED : November 30, 1982

INVENTOR(S) : Shuenn-Tzong Chen

It is certified that error appears in the above-identified patent and that said Letters Patent is hereby corrected as shown below:

On the title page, Inventor's name should read:

-- Shuenn-Tzong Chen --.

Signed and Sealed this

*Fifteenth* Day of *March 1983*

[SEAL]

*Attest:*

*Attesting Officer*

GERALD J. MOSSINGHOFF

*Commissioner of Patents and Trademarks*